US006423009B1

United States Patent
Downey et al.

(10) Patent No.: US 6,423,009 B1
(45) Date of Patent: Jul. 23, 2002

(54) SYSTEM, EMPLOYING THREE-DIMENSIONAL ULTRASONOGRAPHIC IMAGING, FOR ASSISTING IN GUIDING AND PLACING MEDICAL INSTRUMENTS

(75) Inventors: Donal Downey; Aaron Fenster, both of London (CA)

(73) Assignee: Life Imaging Systems, Inc. (CA)

( * ) Notice: Subject to any disclaimer, the term of this patent is extended or adjusted under 35 U.S.C. 154(b) by 0 days.

(21) Appl. No.: 09/308,378

(22) PCT Filed: Nov. 28, 1997

(86) PCT No.: PCT/CA97/00906

§ 371 (c)(1),
(2), (4) Date: Aug. 20, 1999

(87) PCT Pub. No.: WO98/23214

PCT Pub. Date: Jun. 4, 1998

Related U.S. Application Data

(60) Provisional application No. 60/032,059, filed on Nov. 29, 1996.

(51) Int. Cl.[7] .................................................. A61B 8/00
(52) U.S. Cl. .................... 600/461; 600/438; 600/460
(58) Field of Search ................................ 600/459, 462, 600/460, 461; 606/1

(56) References Cited

U.S. PATENT DOCUMENTS

| 5,454,371 A | | 10/1995 | Fenster et al. | |
| 6,027,446 A | * | 2/2000 | Pathak et al. | ................ 600/439 |
| 6,095,975 A | * | 8/2000 | Silvern | ........................ 600/439 |

FOREIGN PATENT DOCUMENTS

| DE | 4010573 | 10/1990 | ............ A61B/17/34 |
| DE | 4225001 | 11/1993 | ............ A61B/5/55 |
| WO | 96/32066 | 10/1996 | ............ A61B/8/14 |

* cited by examiner

*Primary Examiner*—Marvin M. Lateef
*Assistant Examiner*—Maulin Patel
(74) *Attorney, Agent, or Firm*—Katten Muchin Zavis

(57) ABSTRACT

A method and system, employed in combination with a three-dimensional ultrasonographic imaging system, for assisting and placing at least one medical instrument into a prostate during a percutaneous prostrate therapeutic procedure. A process means for determining the spatial relationship between three-dimensional ultrasonographic images of the prostate generated via the transrectal transducer and a reference means. In addition, the method and system assists in guiding and placement of the medical instrument into a target location in the prostate.

22 Claims, 13 Drawing Sheets

SYSTEM, EMPLOYING THREE-DIMENSIONAL ULTRASONOGRAPHIC IMAGING, FOR ASSISTING IN GUIDING AND PLACING MEDICAL INSTRUMENTS

This appln is a 371 of PCT/CA97/00906 filed Nov. 28, 1997 which claims benefit of Prov. No. 60/032,059 filed Nov. 29, 1996.

FIELD OF THE INVENTION

The present invention relates to cryosurgery and more specifically, to a method and system employing three-dimensional ultrasonography for assisting in the placement of cryoprobes and other medical instruments during percutaneous prostatectomy procedures.

BACKGROUND OF THE INVENTION

One of the most important functions of clinical surgery is the resection and removal of undesirable tissues. Cryosurgery is an alternative surgical technique in which undesirable tissue is frozen, in the hope that freezing alone will destroy the undesirable tissue without necessitating resection and removal of the undesirable tissue. Leaving dead tissue in place may have beneficial immunological effects.

Cryosurgery is performed using one or more internally cooled cryosurgical probes which will be hereinafter referred to as cryoprobes. A typical cryoprobe is a surgical device having the general appearance and size of a conventional knitting needle, which is provided with cooling sites disposed at predetermined locations on the outer surface thereof. Typically, the cooling sites are located at the tip of the cryoprobe and cooling is accomplished by employing one of a variety of cooling means such as boiling of refrigerants, cooling of refrigerants, Joule-Thomson effects etc. In a typical percutaneous transrectal cryosurgical procedure, such as a prostatectomy, the cooling site on the cryoprobe is first brought into contact with the undesirable prostate tissue. The cryoprobe is then cooled and, as the temperature of the probe is lowered, tissue freezing begins from the cooling site surface outward into the tissue forming a frozen region commonly referred to as an ice-ball. Typically, freezing is continued until the ice-ball has encompassed all the prostate and any undesirable tissue known to exist outside the prostate. However, as will be described in greater detail below, up until now, the extent of the freezing is usually approximated by the practitioner. The frozen tissue is left in situ to be dealt with by the body's immune system.

In contrast, in traditional resection surgery, the practitioner targets the undesirable tissue and using visual and tactile control, manually resects and removes that tissue.

Cryosurgery has numerous advantages which have promoted small scale, steady use of this procedure for approximately 150 years since the first description of the method by J. Arnott in 1845. Arnott taught that, by applying a brine solution to diseased skin tissue, the tissue could be frozen and destroyed. One of the advantages of cryosurgery is the ease with which this procedure can be applied with minimal trauma to the patient. Conventional surgical procedures require resection which results in blood loss and trauma to the patient.

In modern prostate cryosurgery, cryoprobes are inserted into undesirable tissue through small punctures in the skin at predetermined sites, thereby minimizing the surgical trauma experienced by the patient. In comparison, resection surgery of the prostate is considered a major surgery, with significant bleeding, morbidity, mortality and lengthy recovery periods. There are also further risks and side effects associated with resection surgery such as wound infection, urinary tract infection, deep venous thrombosis, impotence and incontinence.

Another advantage of cryosurgery is that the cryoprobes are applied focally, to treat only the undesirable region, thereby sparing much of the surrounding healthy tissue. This aspect of the procedure has found important applications in liver cryosurgery. In resection surgery, the extent of the tissue removed is determined by many considerations related to conventional resection strategy, such as integrity of the blood supply and the functionality of the tissue remaining after surgery. Often, this strategy requires removal of significant amounts of healthy tissue or even whole organs.

In contrast, the strategy of a cryosurgical procedure is to only remove the undesirable tissue, even if it has irregular margins and shape, leaving the healthy tissue intact. Cryosurgery can therefore be considered a tissue-sparing procedure.

Furthermore, after resection surgery it is often very difficult to retreat the tissue if the disease recurs due to severe fibrosis and the risks of damaging either the sphincter, causing incontinence, or the rectum. However, when cryosurgical procedures are employed, the tissue can be, and routinely is retreated because adhesions and fibrosis considerations are not significant factors. Further to this end, because there is less fibrosis and adhesions in the pelvis, cryosurgery is also advantageous over other modern localized treatment modalities such as, radical prostatectomy, hyperthermia or radiation therapy.

The above-described advantages of cryosurgery have helped the method remain in use for the last 150 years. However, while this type of procedure is effective in many situations where a non-invasive procedure is required, there are several disadvantages with conventional cryosurgical techniques.

Many practitioners were reluctant to use cryosurgery because it was considered inferior to resection surgery. The technique suffered from three major drawbacks which rendered it problematic. Firstly, when the cryosurgical procedure is internal and as no large incisions are made, the practitioner does not have tactile and/or visual contact with the undesirable tissue and is therefore forced to operate "blind". Operating "blind" severely hinders an accurate determination of the outline of the prostate and the extent of any other undesirable tissue. Accordingly, the determination is, at best, only an approximation, based primarily on the practitioner's experience and skill. Secondly, due to the lack of tactile and/or visual contact, the ability to control the extent to which the undesirable tissue is being frozen and thereby destroyed is limited and, once again, must be approximated by the practitioner. Furthermore, the third disadvantage of particular relevance to the present invention is that it is typically very difficult to place medical instruments, such as cryoprobes, percutaneously with any comfortable degree of accuracy. Therefore it is possible that inaccurate placement of the medical instruments could lead to over treatment beyond the desired region, leading to detrimental side effects such as incontinence.

Unlike after resection surgery, after cryosurgery, the undesirable tissue remains in the patient at the end of the procedure. After resection surgery, the practitioner takes confidence in the effectiveness of the procedure in question, by virtue of the fact the undesirable tissue was removed from the patient. However, after a cryosurgical procedure, due to the fact that the undesirable tissue is left in the patient, the level of confidence as to the effectiveness of the procedure is low as there is no true knowledge as to whether or not the undesirable tissue was extirpated. In conventional cryosurgery the practitioner has no means for confirming the success of his procedure immediately at the completion of the cryosurgical procedure. This is also disadvantageous to the patient's psychological state-of-mind, as the patient must recover and wait for further post-surgical testing to determine the effectiveness of the procedure.

The above described disadvantages of cryosurgery were severe enough to make the use of cryosurgery questionable for many years. Probably the most significant breakthrough in cryosurgery occurred when body imaging technologies were developed, and two-dimensional ultrasonography was employed to image the freezing process during cryosurgery. The use of two-dimensional ultrasonography has resolved in part the original drawbacks with cryosurgery and has led to an unprecedented growth in the use of this technique. However, while the use of two-dimensional ultrasonography imaging has alleviated some of the practitioner's above-described visual disadvantage, two-dimensional ultrasonography has not completely resolved the imaging problem. Furthermore, two dimensional imaging does not significantly increase the practitioner's ability to control the extent to which the undesirable tissue is being destroyed in the patient.

Accordingly, there has been a long standing need for an improved method and system, employing three-dimensional ultrasonographic imaging, for assisting in guiding and placing medical instruments during percutaneous prostatectomy which overcomes at least one of the above-described disadvantages of conventional cryosurgical techniques.

SUMMARY OF THE INVENTION

It is an object of the present invention to provide a novel system and method for assisting instrument guidance and placement during a percutaneous cryosurgical prostate therapeutic procedure which obviates or mitigates at least one of the disadvantages of the prior art methods.

According to one aspect of the present invention, there is provided a method employing a three-dimensional ultrasonographic imaging system for determining the placement position of at least one medical instrument in a prostate during a prostate therapeutic procedure, comprising the steps of: i) positioning a reference means relative to a ultrasonographic transducer in a region proximal a site on a patient which facilitates access to the prostate; ii) minimizing relative movement between the reference means and the site; iii) referencing the reference means to the three-dimensional ultrasonographic imaging system to determine the spatial relationship therebetween; iv) obtaining a three-dimensional image of the prostate; v) via a processing means, generating a positioning image by superimposing an image of the reference means over the three-dimensional image; vi) from the positioning image, selecting a target location within the prostate where the at least one medical instrument is to be placed; vii) from the positioning image, determining an insertion path to the target location and determining placement coordinates from the image; and viii) placing the at least one medical instrument into the prostate along the insertion path via the placement coordinates determined from the positioning image.

Steps i) through viii) may be repeated for a plurality of medical instruments.

Preferably, the method includes an additional step, concurrent with steps vi) and vii), of indicating and inputting to the processing means, via a graphical user interface, the target location and insertion path over the positioning image.

Preferably, in accordance with the method of the present invention, the method includes a further step, concurrent with step viii), of monitoring placement of the at least one medical instrument along the insertion path to the target location, via the placement coordinates, with one or more images generated by the three-dimensional ultrasonographic imaging system.

According to another aspect of the present invention there is provided a method of assisting placement of at least one surgical instrument in a prostate during a cryosurgical prostatectomy, comprising the steps of: i) positioning a reference plate relative to a transrectal ultrasonographic transducer in a region proximal a site on a patient which facilitates access to the prostate; ii) securing the reference plate to minimize relative movement between the plate and the site; iii) referencing the reference plate to a three-dimensional ultrasonographic imaging system to determine the spatial relationship between the transrectal ultrasonographic transducer and the plate; iv) obtaining a three-dimensional image of the prostate; v) generating a positioning image by superimposing an image of the reference plate over the three-dimensional image; vi) from the positioning image, selecting a target location within the prostate where the at least one medical instrument is to be placed; vii) from the positioning image, determining a path to the target location via the image of the reference plate and determining placement coordinates from the image; and viii) placing the at least one surgical instrument into the prostate via the reference plate at the placement coordinates determined from the positioning image.

According, to another aspect of the present invention there is provided a system, employed in combination with a three-dimensional ultrasonographic imaging system, for assisting in the placement of at least one medical instrument into a prostate comprising: a reference means; a mounting means for mounting the reference means in a predetermined relationship to a transrectal ultrasonographic probe; the reference means including a plurality of apertures arranged in an predefined manner and sized to permit a medical instrument to pass therethrough; a processing means for determining the spatial relationship between a three dimensional ultrasonographic image of the prostate generated via the transrectal ultrasonographic probe and the reference means; wherein the processing means merges a representation of the plurality of apertures with the three dimensional ultrasonographic image to assist in the placement of the at least one medical instrument in the prostate via an appropriate aperture.

Preferably, in accordance with the system of the present invention, the predefined manner of arranging the plurality of apertures forms a Cartesian coordinate grid.

Alternatively the predefined manner of arranging the plurality of apertures is a polar coordinate grid.

Also preferably, in accordance with the system of the present invention, the mounting means is attached between the transrectal ultrasonographic transducer and the reference means.

Also preferably, the reference means comprises a transparent rectangular plate which is contoured on one side to closely fit a patients perineum.

Also preferably, in accordance with the system of the present invention, the plurality of apertures are provided with an index marking scheme to assist in the identification of placement coordinates and the selected aperture.

Also preferably, in accordance with the system of the present invention, the mounting means includes a transverse adjustment means for adjusting the reference means transversely relative to a long axis passing through the transrectal ultrasonographic transducer.

Also preferably, in accordance with the system of the present invention, the at least one medical instrument is a biopsy needle.

Also preferably, in accordance with the system of the present invention, the at least one medical instrument is a guidance sheath.

Also preferably, in accordance with the system of the present invention, the at least one medical instrument is a cryosurgical probe.

Also preferably, in accordance with the system of the present invention, the processing means forms an integral portion of the three-dimensional imaging system.

Also preferably, in accordance with the system of the present invention, the processing means is a stand-alone computer.

BRIEF DESCRIPTION OF THE DRAWINGS

Presently preferred embodiments of the present invention will now be described, by way of example only, with reference to the accompanying drawings, in which.

DETAILED DESCRIPTION OF THE PREFERRED EMBODIMENTS

In accordance with the present invention, there is provided a method and system, employing a three-dimensional ultrasonographic imaging system for assisting and guiding at least one medical instrument in a prostate during a prostatectomy procedure.

Prior to a detailed discussion of the working principles, components and features of the present invention, a brief discussion of three-dimensional ultrasonography imaging systems will be provided to assist a reader's comprehension of the present invention. The three-dimensional ultrasonographic imaging system presently employed is that disclosed in U.S. Pat. No. 5,454,371, the contents of which are herein incorporated by reference. However as will be understood by those of skill in the art, other three-dimensional ultrasonographic imaging systems may be employed with the system and method of the present invention with equal success.

Figure 1:
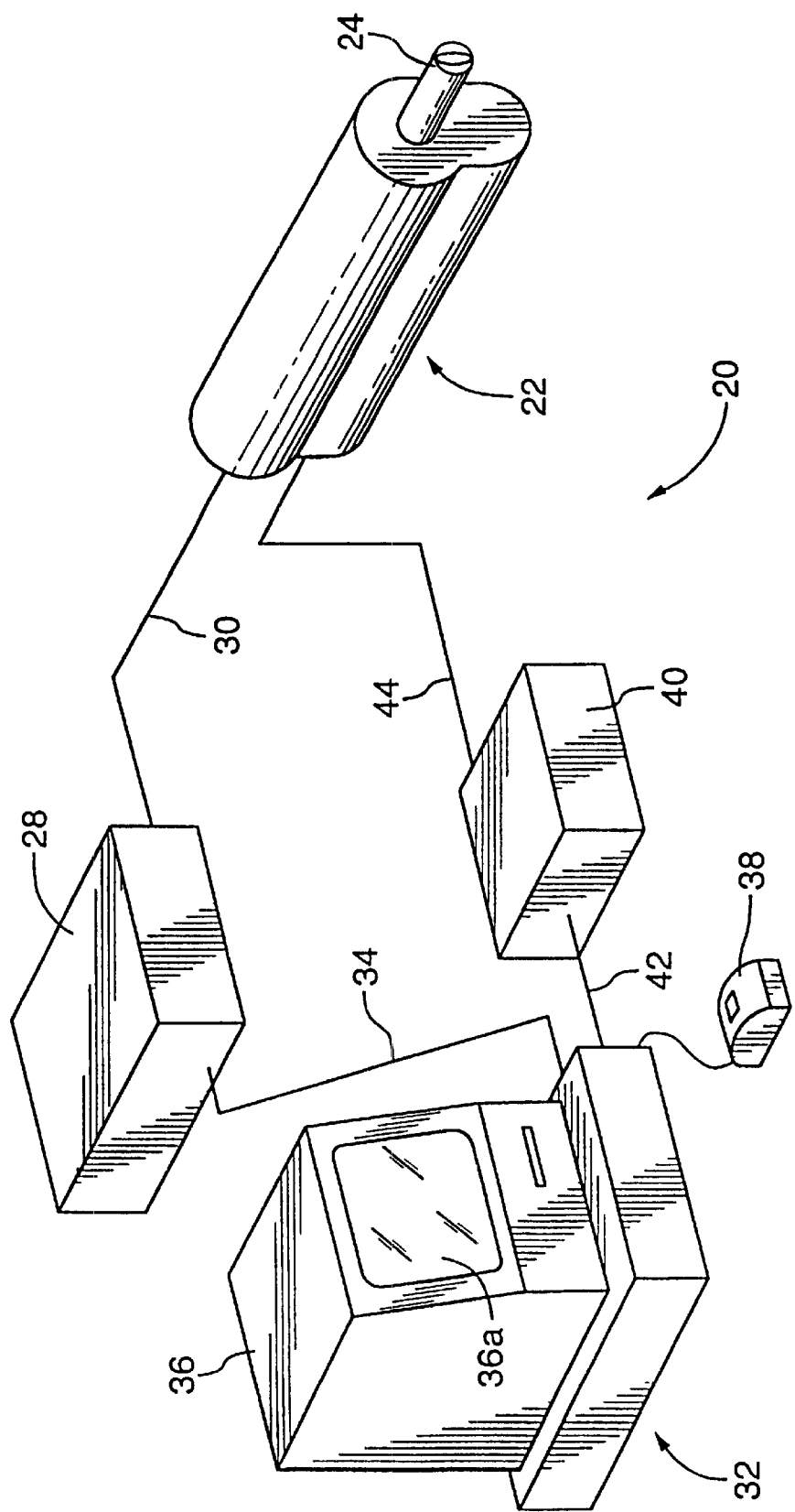
FIG. 1 shows a perspective representation of a three-dimensional ultrasonography imaging system.

Referring now to FIG. 1, the three-dimensional ultrasonographic imaging system is shown and is generally indicated by reference numeral 20. The system 20 is capable of generating a three-dimensional ultrasonographic image of a target volume of a subject under examination from a succession of two-dimensional ultrasonography images of the target volume and allows the generated three-dimensional image to be manipulated. The subject under examination may be inanimate or animate. In the later case, the system 20 may be used in both medical and veterinary environments and may be used as a diagnostic tool or during surgery to provide updated images of the target volume undergoing surgery.

The system 20 includes an ultrasonographic transducer actuating assembly 22 for removably retaining an ultrasonographic transducer 24. The transducer actuating assembly 22 is designed to move the ultrasonographic transducer through a predetermined angular sweep so that a succession of two-dimensional images of the target volume can be taken.

The ultrasonographic transducer 24 is connected to a clinical ultrasonographic machine 28 via a communication line 30. The ultrasonographic machine 28 in turn is connected to a computer 32 via communication line 34. The computer 32 includes a keyboard (not shown), a monitor 36 with a display screen 36a and a graphical input device 38 such as a mouse. The computer 32 provides output signals to a controller 40 via communication line 42 which in turn provides control signals to the transducer actuating assembly 22 via communication line 44.

The ultrasonographic transducer 24, during its sweep, transmits ultrasonographic signals which interrogate the target volume. Reflected ultrasonographic signals from the target volume are also received by the transducer 24 and are converted into analog signals by a crystal (not shown) in the ultrasonographic transducer 24. These analog signals are conveyed to the clinical ultrasonographic machine 28 where a-succession of two-dimensional analog images of the target volume are generated. This operation of the ultrasonographic transducer 24 and clinical ultrasonographic machine 28 is well known to those of skill in the art and therefore, will not be described in any further detail herein.

The two-dimensional analog or digital images generated by the ultrasonographic machine 28 are conveyed to the computer 32 via communication line 34. The computer 32 in turn constructs a three-dimensional image of the target volume from the succession of two-dimensional images. Once the three-dimensional image has been created, the computer 32 allows the three-dimensional image to-be displayed and manipulated.

Figure 2:
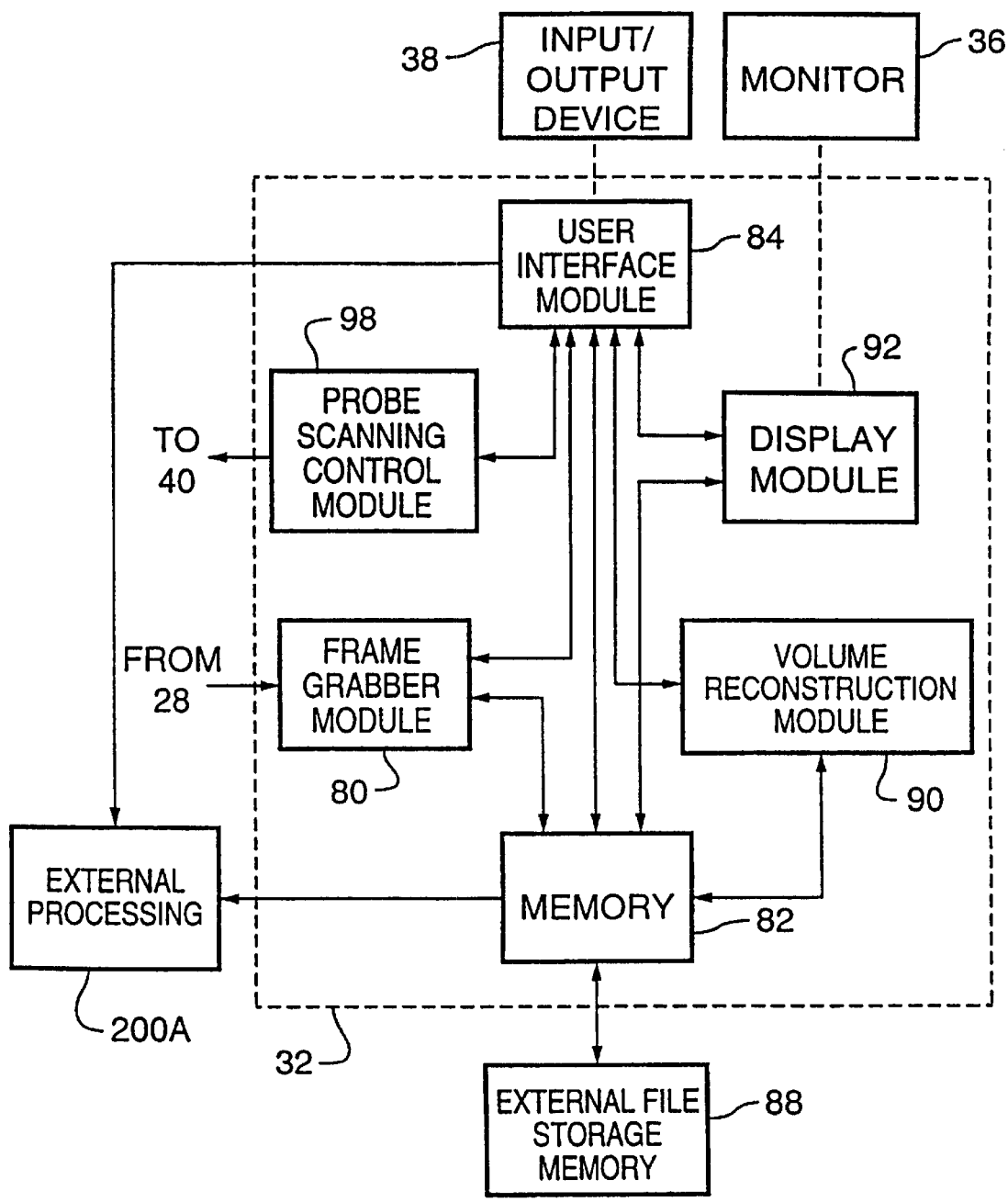
FIG. 2 shows a block diagram of various hardware and software modules of a computer system forming part of the system illustrated in FIG. 1.

Referring now to FIG. 2, once a succession of two-dimensional images of the target volume has been captured and digitized by frame grabber module 80 and stored in the memory 82, the digitized information can be processed in a number of ways depending on the input commands received by the user interface module 84 from the graphical input device 38. Specifically, the digitized information can be transferred to an external file storage memory 88 or transferred to an external processing system 200 for further manipulation. Alternatively, the digitized information can be processed by a volume reconstruction module 90 to form a volumetric image array V (x,y,z) representing a three-dimensional image of the target volume. Once created, the volumetric image array is stored in the external file storage memory 88 or passed to external processor 100 for further manipulation. Alternatively, the volumetric image array may be further processed by a display module 92 in response to input received from graphical input device 38 so that a three-dimensional image of the target volume can be displayed on the screen 36a of the monitor 36 and manipulated as will be described further herein.

The computer 32 also includes transducer scanning control module 98 which provides output signals to controller 40 to actuate the transducer actuating assembly 22 as desired. The transducer scanning control module 98 also receives input from the user interface module 84.

Figure 3A:
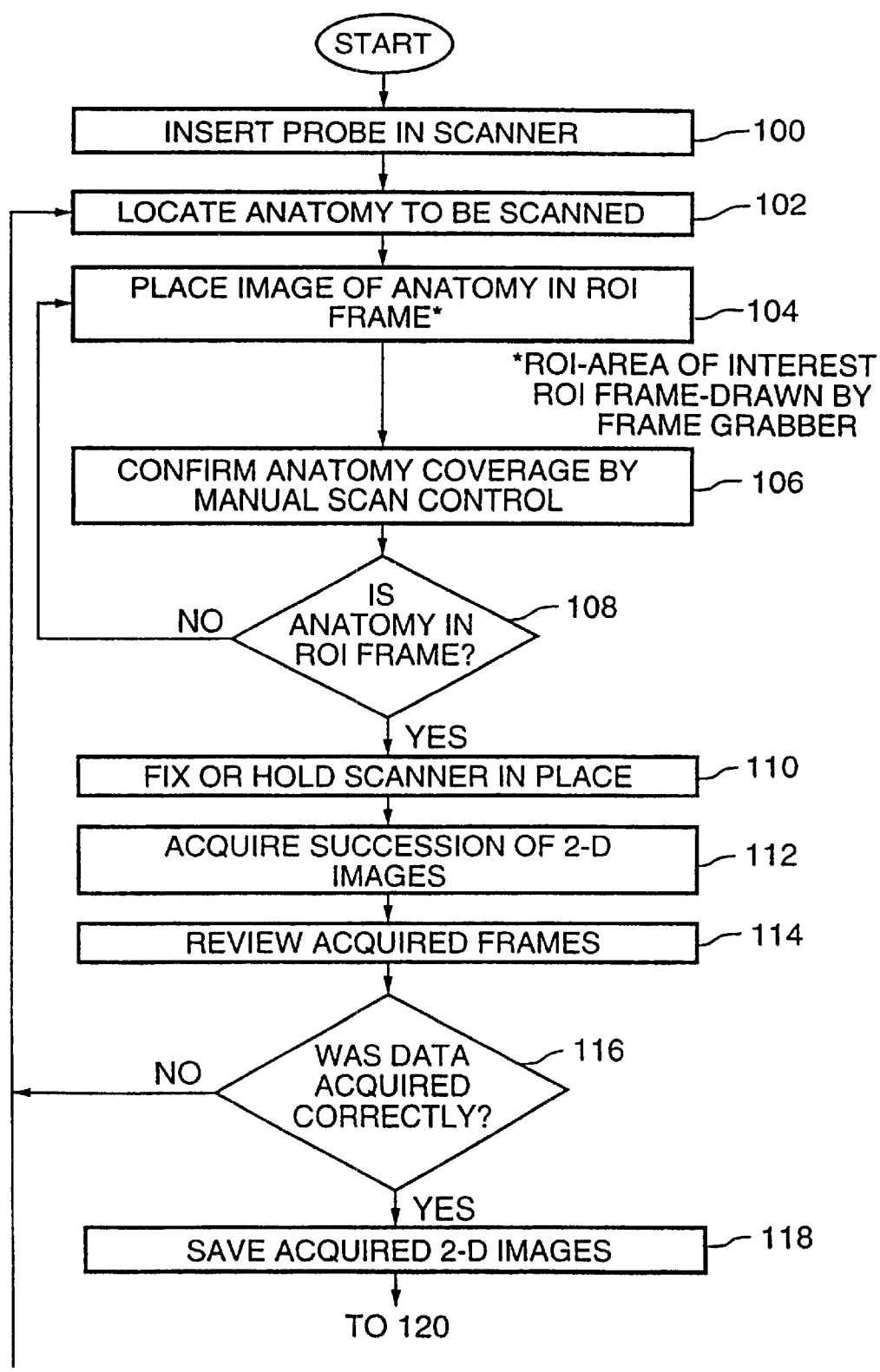
FIG. 3a is a flowchart showing some of the operational steps of the system illustrated in FIG. 1.
Figure 3B:
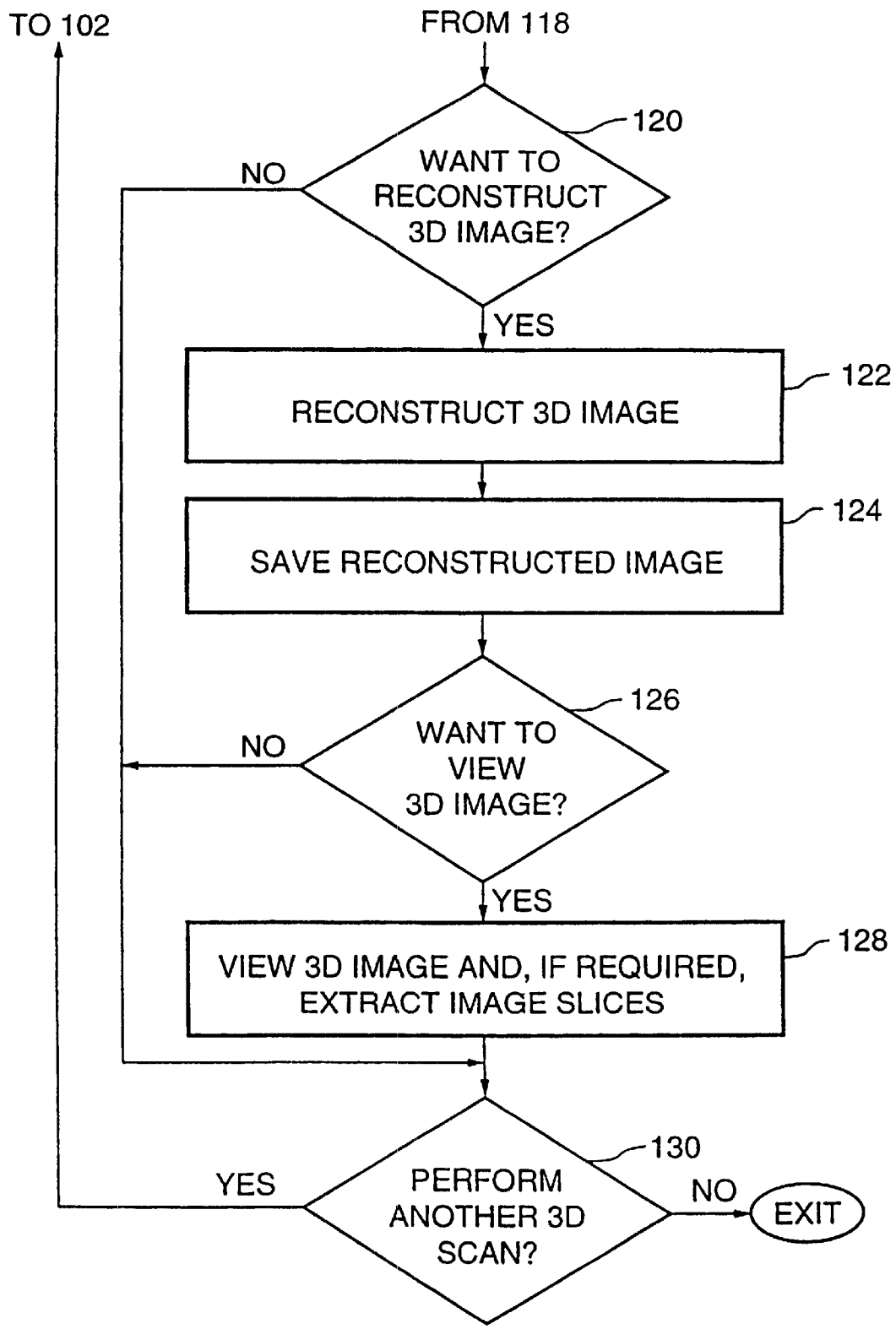
FIG. 3b is a flowchart showing additional operational steps of the system illustrated in FIG. 1.

With reference now to FIGS. 3a and 3b, when it is desired to operate the three-dimensional ultrasonographic imaging system 20 to acquire two-dimensional images of the target volume, the system 20 must be initialized. This requires the ultrasonographic transducer 24 to be positioned in the "probe actuating assembly 22" (see block 100) or referred to as "scanner" in FIG. 3a. Once this is done, the ultrasonographic transducer 24 and transducer actuating assembly 22 must be properly located with respect to the subject so that the ultrasonographic waves transmitted by the ultrasonographic transducer 24 are directed at the target volume (see block 102).

Once the ultrasonographic transducer 24 is positioned, a user inputs a start command by selecting an appropriate icon displayed on the screen 36a using the graphical input device 38. Within the context of the present invention, icon refers to any graphical element displayed on the screen 36a which can be selected using graphical input device 38. When the start command is received by the user interface module 84, the user interface module signals the transducer scanning module 98. The transducer scanning module 98 in turn conveys signals to controller 40 which in turn signals the ultrasonographic transducer 24 to transmit ultrasonographic signals. The reflected ultrasonographic signals received from the target volume are conveyed to the clinical ultrasonographic machine 28 wherein a two-dimensional analog image of the target volume upon which the ultrasonographic signals impinged, is created. The two-dimensional analog image is then conveyed to the computer 32 via communication line 34 wherein it is captured and digitized via frame grabber module 80. The digitized two-dimensional image is then stored in the memory 82.

A copy of the digitized two-dimensional image is then conveyed to the user interface module 84 and the frame is drawn on the screen 36a of the monitor 36 (block 104). The user then manually rotates the transducer 24 while it is transmitting ultrasonographic signals so that two-dimensional analog images generated by the clinical ultrasonographic machine 28 are captured and digitized by the frame grabber module 80. These two-dimensional images are also then drawn on the screen 36a of monitor 36 via user interface module 84 (block 106). Next, the user is prompted to confirm that the ultrasonographic signals are properly directed at the target volume after having viewed the frames drawn on the screen 36a of the monitor (block 108). If the target volume is outside of the drawn frames, then operation returns to block 104. Otherwise, the user provides input to the user interface module 84 using the graphical input device 38 to signify that the target volume is within the drawn frames. Once this has been done and while the transducer actuating assembly 22 is being held in place (either manually or mechanically) (block 110), the user interface module 84 signals the transducer scanning module 98.

At this point in time, the transducer scanning module 98 conveys control signals to the transducer actuating assembly 22 via controller 40 so that the ultrasonographic transducer 24 is rotated while it is transmitting ultrasonographic signals and receiving reflected ultrasonographic signals so that the entire target volume is scanned. As the ultrasonographic transducer receives reflected ultrasonographic signals, it conveys analog information to the clinical ultrasonographic machine 28 which in turn generates two-dimensional analog images. In this manner, a succession of two-dimensional analog images of the target volume representing a volume image are generated by the clinical ultrasonographic machine 28 in response to the output of the ultrasonographic transducer 24 (block 112). The succession of two-dimensional analog images generated by the clinical ultrasonographic machine 28 are captured and digitized by the frame grabber module 80. The digitized two-dimensional images are then conveyed to memory 82 and stored as a stack to form an array of two-dimensional images I(x,y,z) with the pixels in the array I(x,y,z) representing pixels of the digitized two-dimensional images. Because the computer 32 controls the position of the transducer actuating assembly 22 and hence the ultrasonographic transducer 24, the spatial orientation of the individual two-dimensional images relative to the target volume is known.

The two-dimensional images are considered to be grayscale images. However, the technique does not depend on the "colour" of the twodimensional images to function properly. A grayscale pixel is associated with a gray-level having a value between 0 and $(2^n-1)$ inclusively, with n being the number of bits required for storing the gray-levels. The gray-level 0 is usually used as a "background colour" and is said to be Black.

Once the two-dimensional images have been acquired and saved in memory 82 to form array I(x,y,z), the user interface module 84 generates a prompt to signify that this stage of the image capturing has been completed. At this time, the user may review the acquired frames individually in the manner described previously (block 114). If the two-dimensional images have been acquired incorrectty (block 116), the user can condition the system 20 to return to block 102. Otherwise, the acquired two-dimensional images are saved in the external file storage memory 88 (block 118).

Once the two-dimensional digitized images of the target volume have been acquired, the user is prompted to decide whether a three-dimensional image of the target volume is to be reconstructed from the array of two-dimensional digital images I(x,y,z) via volume reconstruction module 90 (block 120). If the user wishes to reconstruct a three-dimensional image, a volumetric image array V(x,y,z) representing a three-dimensional image of the target volume is created from the two-dimensional digital images (block 122). Once created, the volumetric digital image array is saved in external file storage memory 88 (block 124). Afterwards, the user is prompted to decide whether the three-dimensional image is to be displayed on the screen 36a of the monitor 36 (block 126). If the user wishes to view the three-dimensional image, then a copy of the volumetric image array V(x,y,z) is retrieved from the external file storage memory 88 by the display module 92 and is displayed on the screen 36a (block 128). The displayed image can be manipulated by the user as will be described. During image manipulation, the user can store displayed views in the memory 82 or in the external file storage memory 88 so that these views can be retrieved and reexamined at a later time. Once image manipulation has been completed, the user is prompted to confirm whether another three-dimensional image is to be created (block 130). If the user wishes to create another three-dimensional image, the system 20 reverts to block 102. Otherwise, the three-dimensional imaging procedure is considered to be completed.

If at block 120, the user does not wish to reconstruct a three-dimensional image, or if at block 126, the user does not elect to view the reconstructed three-dimensional image, the system proceeds directly to block 130.

Percutaneous Transrectal Ultrasonographic Guided Cryosurgery

Figure 4A:
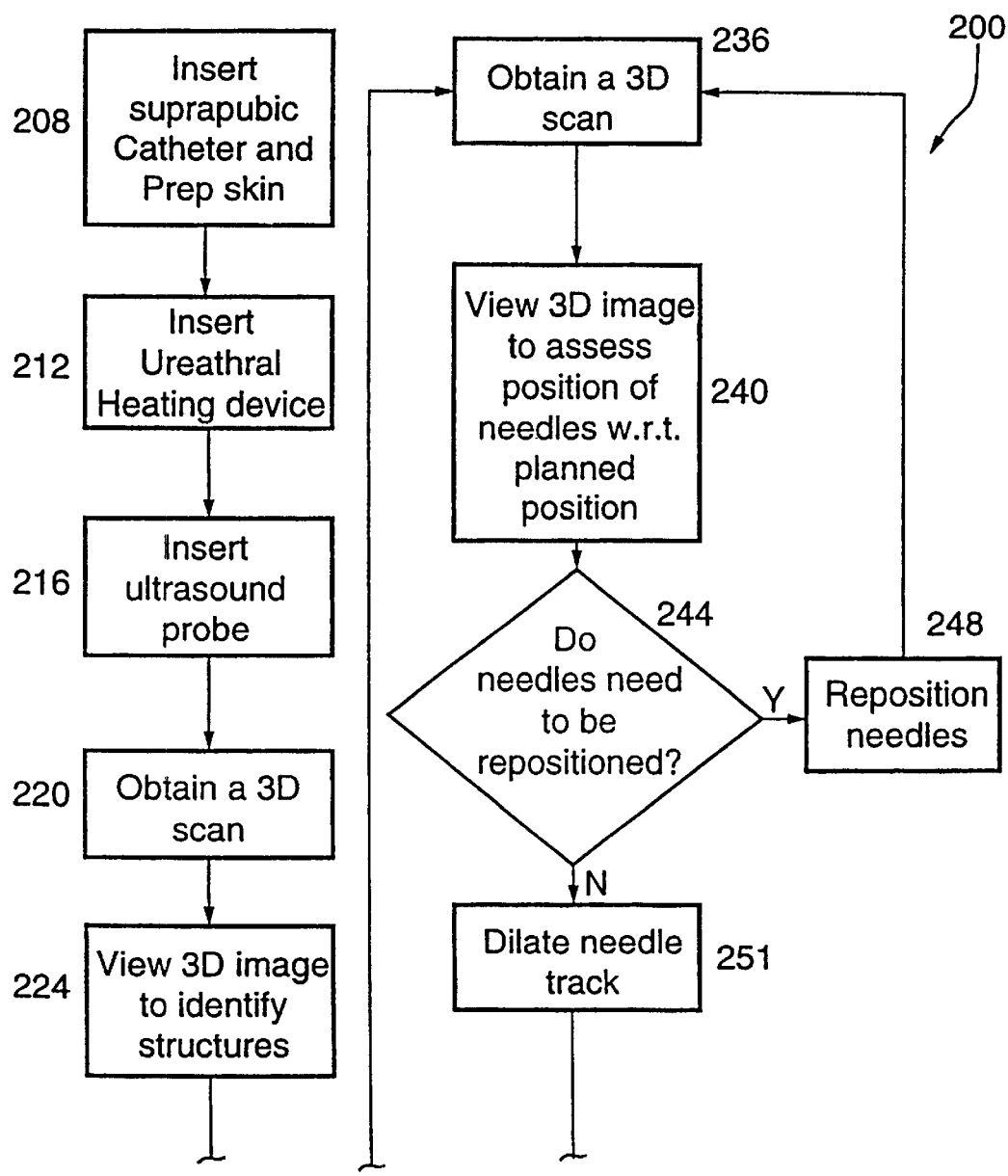
FIG. 4a is a flowchart showing some of the operational steps for performing a cryosurgical procedure using the system illustrated in FIGS. 1 and 2.
Figure 4B:
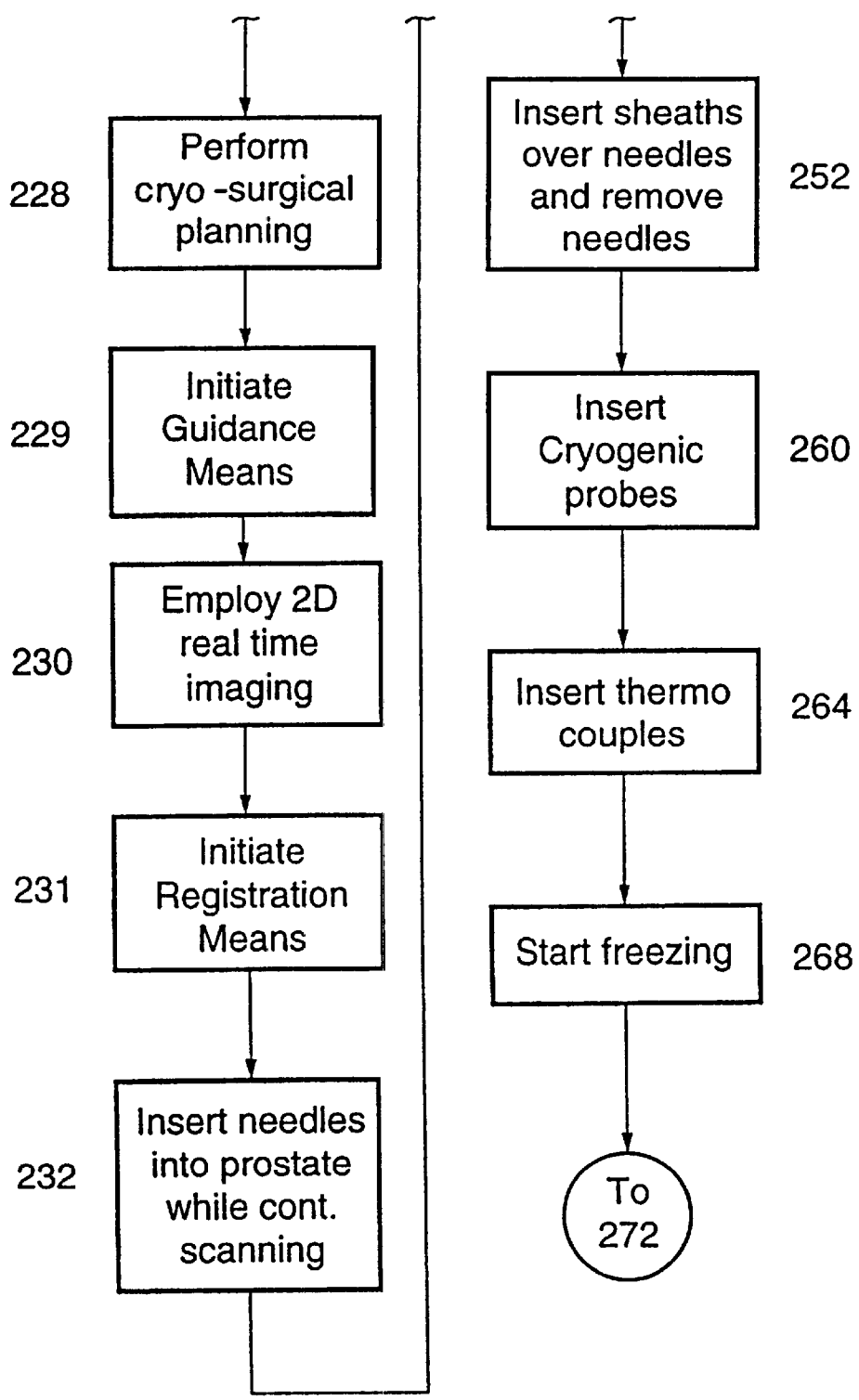
FIG. 4b is a flowchart showing additional operational steps for performing a cryosurgical procedure using the system illustrated in FIGS. 1 and 2.
Figure 4C:
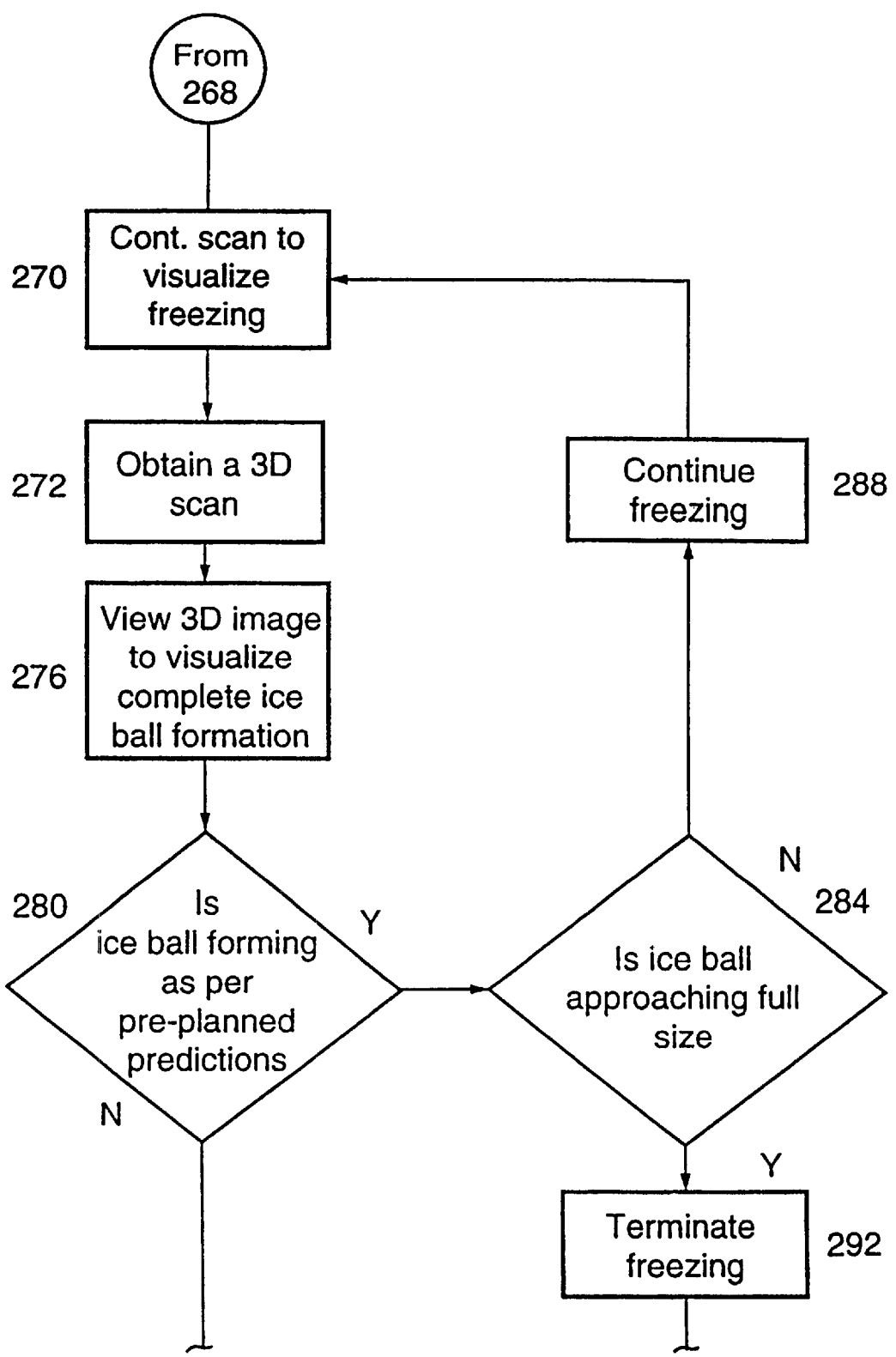
Figure 4D:
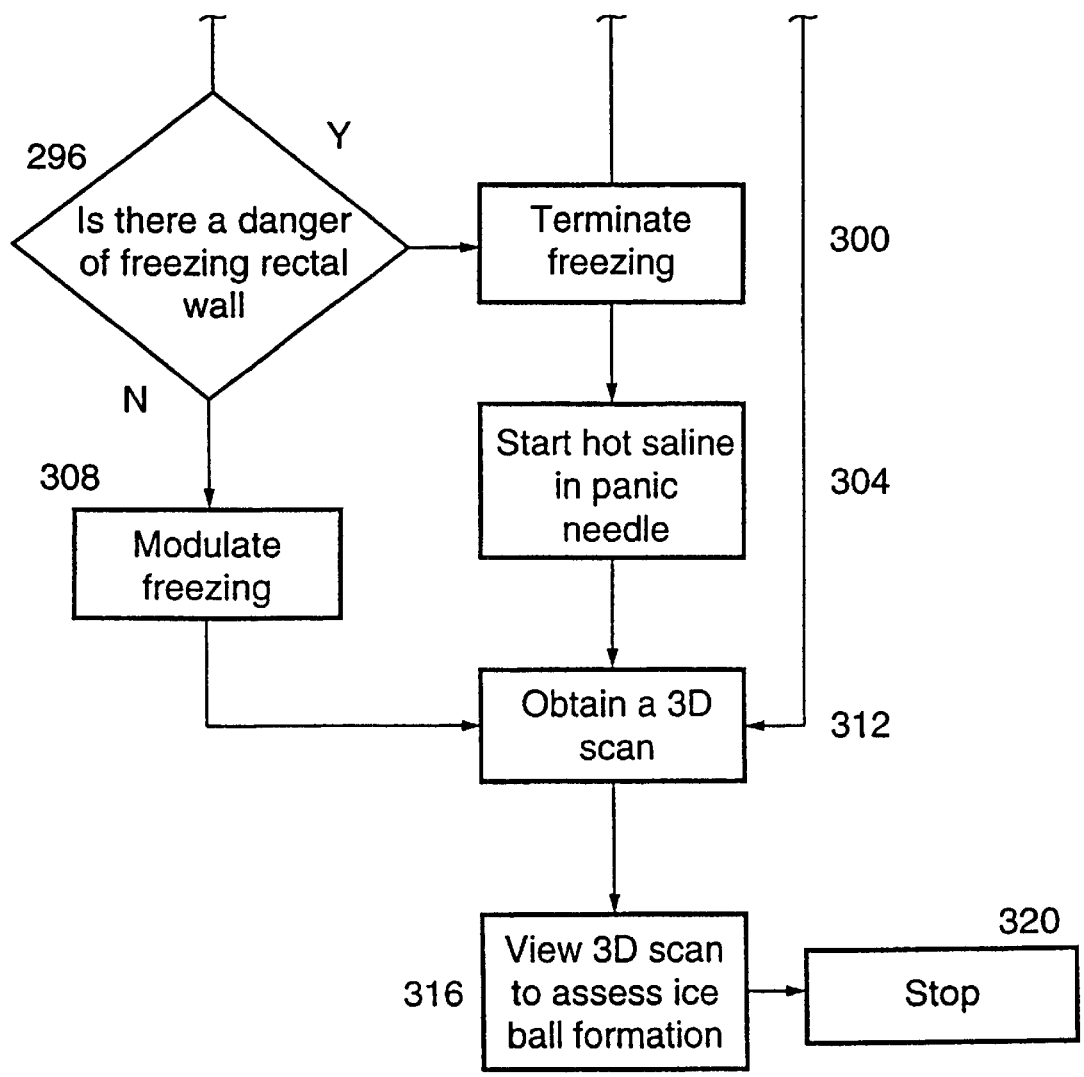

A block diagram of a cryosurgical method in accordance with one embodiment of the present invention is illustrated in FIGS. 4a through 4c and is indicated generally at 200. While the present invention has applications in various tissues and cryosurgical applications, the present inventors have applied the system and method of the present invention successfully to percutaneous transrectal ultrasonographic (TRUS) guided prostate cryosurgery as described herein.

During TRUS guided prostate cryosurgery, the first step in preforming the cryosurgical method is indicated at block 204 in which the practitioner inserts a suprapubic catheter into the patient and prepares the skin for cryosurgery. A urethral heating device is then inserted into the catheter (block 212) for the purposes of protecting the urethra from freezing. Transrectal ultrasonographic transducer 24 is then inserted into the rectum of the patient (block 216) and a scan is obtained using three-dimensional ultrasonographic imaging system 20 (block 220), following the procedure as indicated in FIGS. 3a and 3b described above. The practitioner then views the image to identify the structures in view (block 224). Specifically, the practitioner identifies regions such as fat, prostate tumour, highly vascularized regions, possible needle insertion points etc. Based on information available from the image generated by three-dimensional ultrasonographic system 20, the practitioner performs cryosurgical preplanning (block 228) to determine, amongst other parameters, the number of cryoprobes to be employed, the insertion point(s) and the location(s) within the prostate of the cooling surfaces of the cryoprobes.

The cryosurgical pre-planning 228 may be accomplished manually whereby the practitioner exercises his skill, drawing upon knowledge of the size of the tumour, the regions previously identified and knowledge of the cryoprobes employed. Pre-planning of the cryosurgical procedure is useful for assisting the practitioner in improved placement of the cryoprobes and for monitoring of the freezing process. Currently, practitioners of cryosurgery use the above described two-dimensional and three-dimensional ultrasonographic images to guide cryosurgical transducer into the centre of the tissue that they desire to destroy. During a cryosurgical procedure, at least one cryoprobe is employed in the expectation that the resulting shape of the ice ball will encompass the undesirable tissue area. However as previously mentioned, the choice of the placement of these transducers is usually based on experience and skill of the practitioner. As the operating, prostate, and patient conditions of each cryosurgical procedure are never the same twice, the manual method of cryoprobe placement would benefit from additional assistance, namely a guidance means. Furthermore, the practitioner is still required to rely on his experience to visualize in 3D the spatial relationship to the target when guiding and placing the medical instruments.

Figure 5:
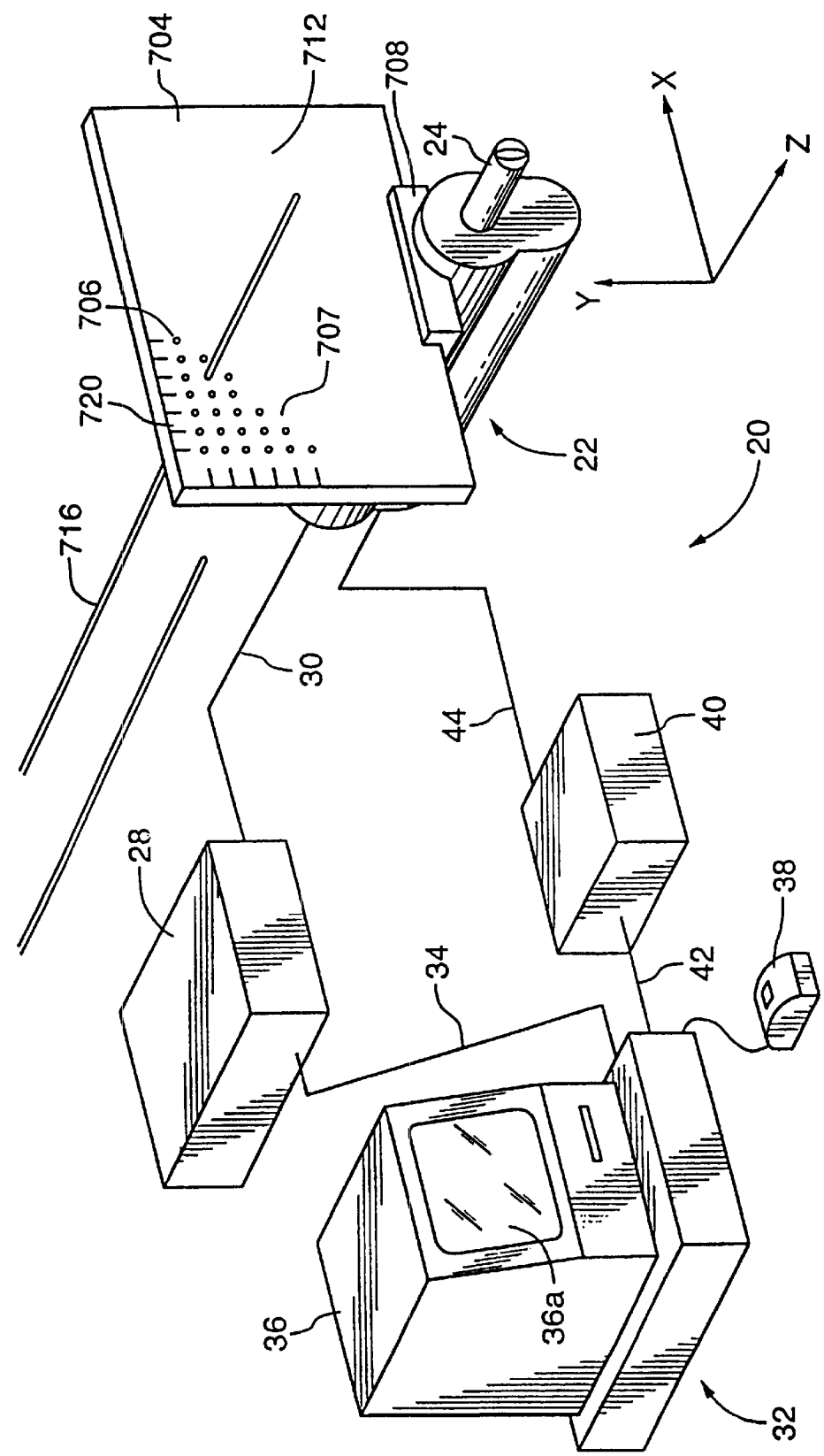
FIG. 5 shows a system for guiding and placing instruments during a cryosurgical procedure in accordance with an embodiment of the present invention.

Accordingly, FIG. 5 shows an system for assisting in the placement of the medical instruments. The system generally comprises a reference means, which in the present embodiment is in the form of a reference plate 704, movably attached to transducer actuating assembly 22 via a mount means 708. Reference plate 704 is provided with a plurality of small, regularly spaced apertures 706 which form a Cartesian grid coordinate system 707. The plurality of apertures pass through reference plate. 704 orthogonal to a face plane 712 and are sized to allow at least one medical instruments such as a biopsy needle 716 to pass therethrough. The Cartesian grid of apertures 706 is further provided with an indexing means 720 which facilitates the practitioner in the placement of the at least one medical instrument 716. Typically, the indexing means is in the form of alphanumeric markings on face plane 712 indicating the rows and columns of apertures forming the Cartesian grid. It is further contemplated that the Cartesian grid of apertures 706 could be replaced with a Polar coordinate grid structure and achieve similar results. Accordingly, in this case, indexing means 720 would be altered to indicate radius and degrees.

Mounting means 708 is preferably fixedly attached to transducer actuating assembly 22 so as to establish a reference location between transducer 24 and reference plate 704. Mounting means 708 preferably includes an adjustment means (not shown) such that face plane 712 can be adjusted transversely with respect to transducer 24 such that a projection of at least a portion of the grid of apertures 706 maps onto the target location.

It is contemplated that a plurality of orientation sensors (not shown) could be included on mounting means 708 which measure the orientation of face plane 712 in the X, Y, and Z planes with respect to the longitudinal axis of transducer 24. The orientation sensors would be-connected to computer 32 and would provide feedback to preplanning block 228 for improved needle placement.

In operation, once transducer 24 has been placed in the patient, the system is initialized so that the orientation of face plane 712 and a reference aperture (not shown) on Cartesian grid 707 is referenced to transducer 24 and the three-dimensional image displayed at block 224. At this point, an digital image representation of the Cartesian coordinate grid is superimposed over the three-dimensional image such that the grid of apertures 706 spatially correspond with the imaged region.

The practitioner then determines the desired target location for the at least one medical instrument 716, and inputs this information to the system The system then calculates the trajectory path of insertion in three dimensions via an appropriate aperture in reference plate 704. The results of this calculation are communicated to the practitioner through one of several possible means. Typically the results are displayed on monitor 32a by highlighting or changing the colour of the selected aperture on the positioning image or, display the appropriate index coordinates. The planned trajectory may be viewed in three dimensions from many different perspectives. If more than one medical instrument 716 is required for insertion into the prostate, the foregoing steps may be consecutively repeated for each instrument or, the plurality of target locations may be entered as a single step.

When the at least one medical instrument 716 is inserted through the indicated aperture, into the patient as that indicated in block 232 of FIG. 4a, the path of the instrument can be monitored using real-time two-dimensional ultrasonographic imaging as previously describe. Further to this end, the calculated path of the at least one medical instrument 716 can be superimposed over the real-time image to assist the practitioner. If the calculated trajectory path of the at least one medical instrument 716, to the target, is at an oblique angle to face plane 712, reference plate 704 could be moved, under the guidance of the previously described orientation sensors, such that the orientation of face plane 712 is perpendicular to the calculated trajectory path.

Upon the practitioner confirming the planned trajectory for the medical instrument, the transducer actuating assembly may automatically rotate the transducer to view the inputting of the needle on two dimensional scanning.

In an alternative embodiment, a frameless stereotaxis system is employed for assisting in the placement of the instruments. As indicated above, once preplanning block 228 is accomplished and the three-dimensional model is tracking the real-time two-dimensional image to compensate for organ movement, instrument placement can occur. However, in this situation, the frameless stereotaxis system is the reference means which provides feedback to the practitioner as to instrument orientation in three space without necessitating the use of the previously described reference frame 704.

In practice, the insertable portion of the at least one medical instrument such as the biopsy needle would be provided with a tracking means. A sensing means is then established proximal the surgical site. The sensing means could include for example, a magnetic field which is generated in or about the patient and encompasses the path from the insertion point to the target location. Computer 32 then superimposes a three-dimensional grid coordinate system through the target volume which in this case is the prostate. Computer 32 then assigns or maps coordinate locations for each optimal target location of each needle calculated in preplanning block 228 onto the grid. The practitioner is then provided with instructions as to how to direct each needle.

For example, display screen 36a could instruct the practitioner to direct needle number 1, 26° in the X-plane and 40° in the Y-plane. The needle is then inserted manually by the practitioner while the frameless stereotaxis system tracks the trajectory of the needle by sensing the insertion point location within the magnetic field. If the needle deviates from the trajectory, an alarm triggers, indicating to the practitioner either audibly or visually that he is directing the needle off course. Computer 32 could also provide information to the practitioner on how to correct the trajectory. It is further contemplated that the frameless stereotaxis system could, by supplying the coordinates of each insertion point of each needle, plot the actual paths traversed on display screen 36a, with the optimal paths.

It is further contemplated that a target point could be designated on the three-dimensional reconstructed ultrasonographic image. In this alternative embodiment, computer 32 is further connected to a robotic controller (not shown) which controllers a robot having at least three degrees of freedom. The robot is fitted with a gripper assembly adapted to removably retain and guide the at least one medical instrument such as the previously described biopsy needles, sheaths, cryoprobes and thermocouples. As the target moves on the real-time ultrasonography, compensating translations are calculated and the robotic arm, placing the instrument moves along a trajectory which is continuously being updated with the relative translations caused by the organ movement.

Referring back to FIG. 4a, a real-time two-dimensional ultrasonographic imaging is now employed as a placement guidance means (block 229) to assist the practitioner in placement of the at least one medical instrument 716 (block 232) prior to insertion of the actual at least one cryoprobe. For the remainder of the discussion, medical instrument 716 will be identified by the specific instrument as dictated by the discussion however, as is understood by one of skill in the art, medical instrument 716 is not meant to be limited to specific instruments identified in this discussion.

Typically, organ or tissue movement is usually a concern at this point during the procedure. In particular, normal patient respiration will cause most organs such as the prostate to translate and therefore move out of registration with the previously acquired three-dimensional image. As mentioned, when needles are inserted into the prostate, the practitioner is doing so under the guidance of real-time two-dimensional ultrasonography however, the practitioner is relying on a path determined by the three-dimensional image which may be out of registration with the corresponding plane of the real-time two dimensional image. Therefore, prior to insertion of needles into the prostate (block 232) a registration means (block 231) may be optionally employed which registers the model with the real-time two dimensional image to compensate for the organ movement and assist in needle guidance. The method of employing the registration means is described in greater detail below.

Once the registration means (block 231), when employed, registers the prostate with the model, the practitioner then inserts needles into the prostate (block 232) at the locations determined at block 228, under placement guidance means 229 with real-time two-dimensional ultrasonography via clinical ultrasonographic machine 28 operating in the bi-plane mode. Once the needles are in position, another three-dimensional scan is obtained (block 236) and viewed at block 240 to determine the three-dimensional spacial orientation of the needles in the prostate. A decision is then made (block 244) as to whether the needles are in their required position. If the needles are placed incorrectly, the practitioner then repositions the needles (block 248) and proceeds back to blocks 236 and 240 to assess the positioning three-dimensionally.

If the needle positions are correct, the needle tracks are dilated (block 251) and sheathes are inserted over the needles (block 252). The needles are then removed from the sheathes and cryoprobes are inserted in their place (block 260) again under the guidance of real-time two-dimensional images generated by clinical ultrasonographic machine 28 operating in the bi-plane mode. At this point, a plurality of thermocouples are also inserted at different points adjacent to the prostate, to monitor the freezing process (block 264). The thermocouples are connected to a display means for monitoring temperature within and adjacent to the prostate.

Once the above-described steps have been accomplished, the cryoprobes are activated and freezing of the prostate commences (block 268). During the freezing, real-time two-dimensional images are employed to monitor the formation of the ice ball (block 270). Concurrent with the freezing step, another three-dimensional scan is obtain to monitor cryobalation in three dimensions (blocks 272 and 276). From this updated three-dimensional image, together with thermal data acquired from the thermocouples, cryobalation is assessed by the practitioner. If the ice ball is forming as thought by the practitioner (block 280), and if the ice ball is not approaching its full size, (block 284) freezing continues (block 288) and the process loops back to block 272 where another three-dimensional scan is obtained to monitor the continued ice ball formation. The continued freezing cycle at block 288 is once again monitored by real-time two-dimensional images from clinical ultrasonographic machine 28.

If at block 280, cryobalation has deviated from that predicated or if the practitioner is losing control of the procedure but there is little or no danger of freezing the rectal wall (block 296), the freezing process (block 308) may be adjusted accordingly. The process returns to block 272 where the above described three-dimensional viewing and freezing monitoring is repeated.

On the other hand, if at block 296, the practitioner or the workstation determines that there is a danger that the rectal wall may be damaged by the freezing process, the freezing is terminated (block 300).

If at block 284, it is determined that the predefined ice ball boundary is being approached by the actual ice ball formation, the freezing can be terminated (block 292). It should be noted that ice ball formation does not terminate once the freezing is terminated. By the very nature of commonly understood thermodynamic principles, properties of the patient's tissue and operating conditions, ice ball growth is transient and will continue for a period of time after the cryoprobes are turned off. Therefore, to determine the final extent of ice ball formation, another three-dimensional scan is obtained via system 20 and viewed by the practitioner (blocks 312 and 316) to assess the final formation in three dimensions.

Method for Organ Movement Compensation for 3D Ultrasonography

A significant limitation to the use of three-dimensional ultrasonography for guidance of interventional procedures, which includes the previously described TRUS prostate cryosurgery, is the effect that moving organs have on the accuracy of instrument placements. As previously described, three-dimensional ultrasonographic system 20 operates by having computer 32 reconstruct a three-dimensional model of the target volume being scanned. This model is reconstructed-by summating multiple two-dimensional plane scans which are acquired by a sweep of ultrasonographic transducer 24 under the control of computer 32 and controller 40.

When scanning moving organs the patient is usually asked to hold his breath thereby minimizing organ movement so that data from each two-dimensional plane acquired is in correct spatial relationship to the data obtained from other planes. However, there is no assurance that the reconstructed three-dimensional model will be in the correct spatial relationship to the organ due to the movement experienced by respiration. This situation therefore makes three-dimensional ultrasonography difficult to be used as a guidance means in which the target volume (in the present example, and organ) changes its position after the data is acquired.

Figure 6A:
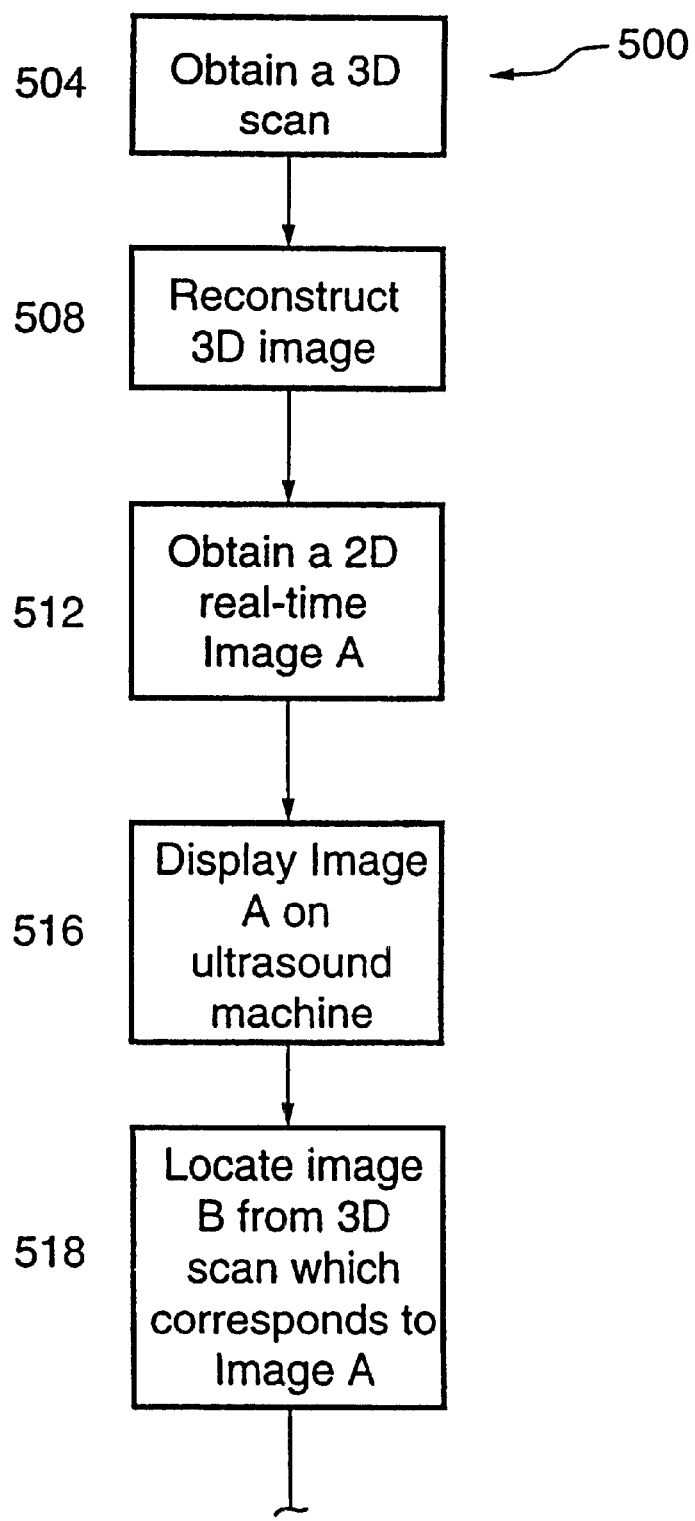
FIG. 6 is a flowchart showing some of the steps for compensating for organ movement between a three-dimensional model and a real-time three-dimensional image in accordance with an embodiment of the present invention; and, FIG. 7 is a flowchart showing some of the steps for compensating for organ movement between the three-dimensional model and the real-time three-dimensional image in accordance with another embodiment of the present invention.
Figure 6B:
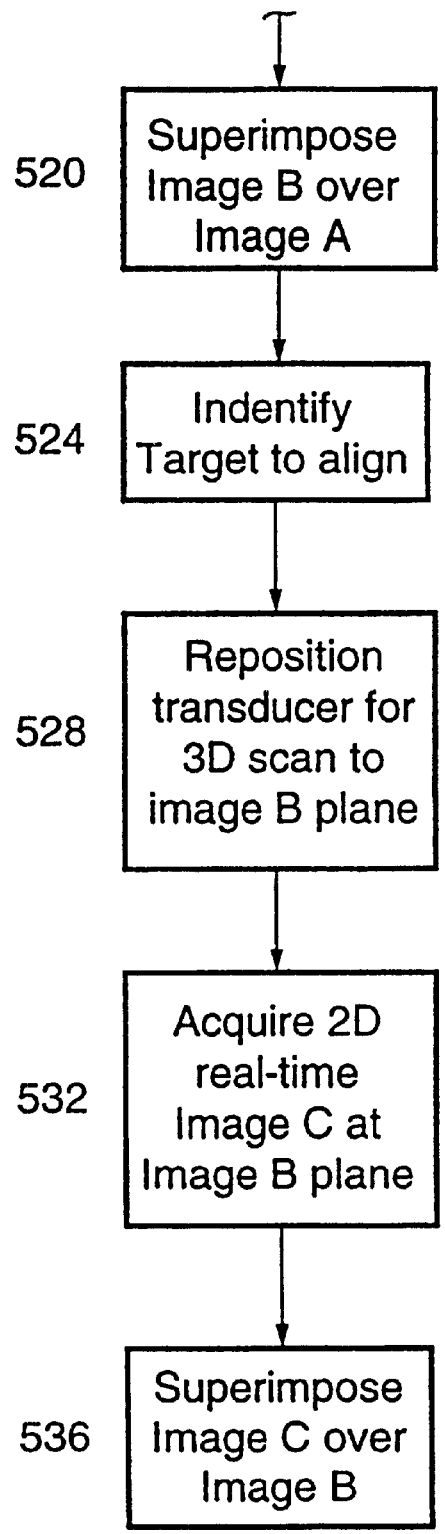

A block diagram of a method of compensating for movement of a target volume is illustrated in FIG. 6 in accordance with another embodiment of the present invention is indicated generally at 500. The first step in the method is to obtain a two-dimensional scan and reconstruct a three-dimensional image (block 504 and 508). During the cryosurgical procedure previously described with respect to FIG. 4, the process of obtaining the scan and reconstructing the image (blocks 504 and 508) is accomplished at blocks 220 and 224.

As indicated in the discussion with respect to FIG. 1, the reconstructed three-dimensional image is displayed on display screen 36a. Ultrasonographic transducer 24 is repositioned to acquire a real-time two-dimensional image A of the target volume (block 512). Image A is then displayed on clinical ultrasonographic machine display 28a (block 516) and represents a two-dimensional image in a single plane. A corresponding two-dimensional image B from data previously obtained with respect to the three-dimensional reconstruction is then superimposed on screen 28a over the real-time image A (block 520) or is displayed on a separate display (not shown). The practitioner views images A and B to identify the target T that he or she wants to hit (block 524).

Ultrasonographic transducer 24 is then brought back to the plane of image B by computer controller 40 operating in communication with actuating assembly 22 (block 528). A new image C is then acquired in this plane on which the target T is displayed on clinical ultrasonographic machine 28a, as a real-time two dimensional image (block 532), Image C will in all likelihood be skewed due to movement of the organ. By definition when image C matches image B acquired from the two-dimensional scans used to reconstruct the three-dimensional image, the organ is again in the same position that it was in when the original three-dimensional data was acquired. While these two matching ultrasonographic pictures B and C may be shown on two different displays, to facilitate alignment, it is contemplated that the images the two pictures could be overlayed on the same screen 28a, thereby assuring that there is alignment of the images (block 536).

As long as the patient holds his or her breath when the two pictures are correctly overlaid, the organ will be in the correct position. As previously described and as shown in FIG. 5, guidance means, such as frame and/or frameless stereotaxis methods and systems, can be used to display the position of the instruments on the three-dimensional model. As the at least one medical instrument approaches the target T, the position can be confirmed in real-time by the appearance of the cryoprobes on the two-dimensional real-time ultrasonographic image displayed An alternative embodiment of the present invention representing the method of compensating for organ movement is indicated generally at 600 in FIG. 7. In this embodiment, the method of compensating for organ movement may be further simplified for the practitioner by designating a group of characteristic pixels in the two-dimensional real-time image C. Once again, a three-dimensional scan and reconstruction is obtained (blocks 604 and 608). A two-dimensional real-time image D is then obtained (block 612). A two-dimensional image E from a plane image acquired from the scan obtained at block 604 is found (block 616) and images D and E are superimposed on display 36a (block 620). As image D is real-time, the practitioner can watch the target moving. At the time when real-time image D move into registration with image E, the practitioner clicks on the pixels representing an area of interest on the images (block 624). Selecting these pixels thereby establishes a reference between images and therefore, the three-dimensional model is now indexed through the reference pixels in plane image E. Computer 32 can then track the movement of these designated pixels (block 628). The designated pixels moving with respect to two-dimensional real-time image D, displayed on monitor display 36a, are tracked in both the X and Y directions by computer 32. The relative position of the three-dimensional model is then translated to the shifted coordinates indicated by the real-time tracking of the designated pixels in image D.

This is an improvement over the embodiment of FIG. 6 in that in the present embodiment, the matching of real-time image with the model needs to occur only once. If the patient has to resume respiration before the instruments being guided has reached the target, the patient can stop respiration at any level without the practitioner having to re-register the two pictures, since the position of the model is updated automatically.

In is further contemplated that three-dimensional reconstruction of other imaging modalities such as Computer Tomography (CT) or Magnetic Resonance Imaging (MRI) can be used in addition to, or as a replacement for, the three-dimensional ultrasonographic model. In this embodiment ultrasonographic transducer 24 is manoeuvred until a real-time two-dimensional ultrasonographic image D is produced of a plane showing characteristic landmarks of the organ anatomy or the target. This plane is then found in a three-dimensional model generated using the CT or MRI modalities and image E is generated. When the two-dimensional real-time ultrasonographic image D matches that of the three-dimensional model image E, the characteristic pixels are designated. These reference pixels can again be tracked on computer 32 to allow reorientation of the three-dimensional MRI or CT model to the new organ position.

Figure 7A:
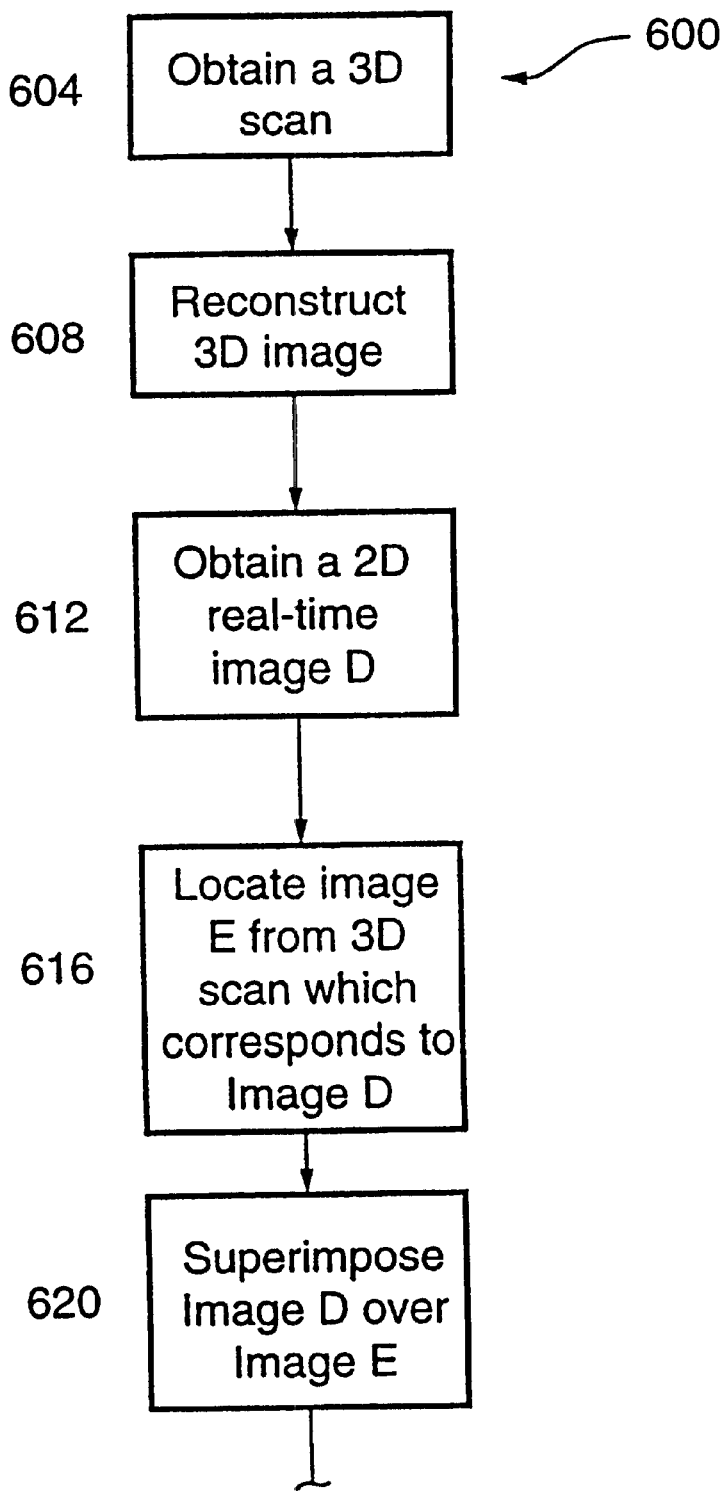
Figure 7B:
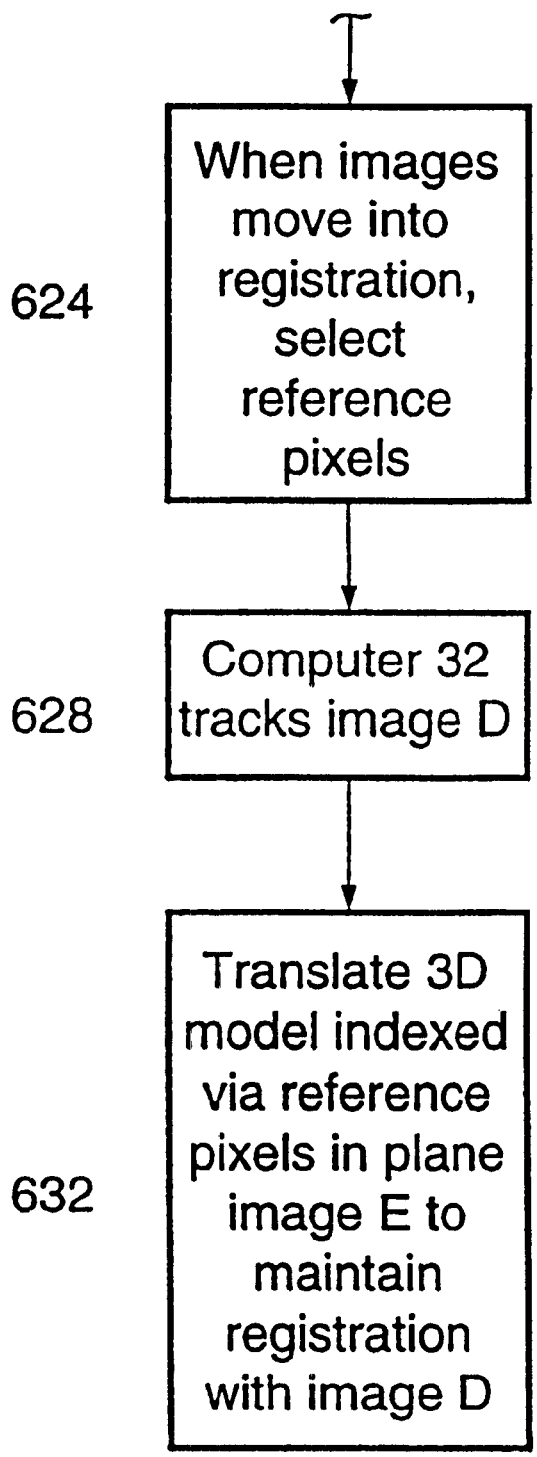

All of the above described methods, such as those illustrated with respect to FIGS. 6 and 7, assume the movement of the organ in question will occur along the long axis of the ultrasonographic transducer. In a third alternative embodiment of the method for compensation of organ movement, it is contemplated that by using dedicated a high speed computer workstation, the three-dimensional reconstructed model can be generated at or sufficiently close to real-time. In this case, three-dimensional ultrasonography can be used as the reference to which the three-dimensional MRI or CT model can be oriented. It is contemplated that this could allow orientation of the three-dimensional model in the Z direction (third axis). The high speed computer workstations could comprise dedicated workstations operating in parallel, multiple processor workstations or a main frame computer.

The present invention has been described with reference to presently preferred embodiments. Other variations and embodiments of the present invention may be apparent to those of ordinary skill in the art. Accordingly, the scope of protection sought for the present invention is only limited as set out in the attached claims.

What is claimed is:

1. A method employing a three-dimensional ultrasonographic imaging system for assisting and guiding the placement of at least one medical instrument in a prostate during a prostate therapeutic procedure, comprising the steps of:
    i) positioning a reference means relative to a ultrasonographic transducer in a region proximal a site on a patient which facilitates access to the prostate;
    ii) minimizing relative movement between the reference means and the site;
    iii) referencing the reference means to the three-dimensional ultrasonographic imaging system to determine the spatial relationship therebetween;
    iv) obtaining a three-dimensional image of the prostate;
    v) via a processing means, generating a positioning image by superimposing an image of the reference means over the three-dimensional image;
    vi) from the positioning image, selecting a target location within the prostate where the at least one medical instrument is to be placed;
    vii) from the positioning image, determining an insertion path to the target location and determining placement coordinates from the image; and,
    viii) placing the at least one medical instrument into the prostate along the insertion path via the placement coordinates determined from the positioning image.

2. The method according to claim 1 wherein, steps i) through viii) are repeated for a plurality of medical instruments.

3. The method according to claim 1 wherein, the method includes an additional step, concurrent with steps vi) and vii), of indicating and inputting to the processing means, via a graphical user interface, the target location and insertion path over the positioning image.

4. The method according to claim 1 wherein the method includes a further step, concurrent with step viii), of monitoring placement of the at least one medical instrument along the insertion path to the target location, via the placement coordinates, with one or more images generated by the three-dimensional ultrasonographic imaging system.

5. A method of assisting placement of at least one surgical instrument in a prostate during a cryosurgical prostate therapeutic procedure, comprising the steps of:
    i) positioning a reference plate relative to a transrectal ultrasonographic transducer in a region proximal a site on a patient which facilitates access to the prostate;
    ii) securing the reference plate to minimize relative movement between the plate and the site;
    iii) referencing the reference plate with a processing means in communication with a three-dimensional ultrasonographic imaging system to determine the spatial relationship between the transrectal ultrasonographic transducer and the plate;
    iv) obtaining a three-dimensional image of the prostate;
    v) generating a positioning image by superimposing an image of the reference plate over the three-dimensional image;
    vi) from the positioning image, selecting a target location within the prostate where the at least one medical instrument is to be placed;
    vii) from the positioning image, determining a path to the target location via the image of the reference plate and determining placement coordinates from the positioning image; and,
    viii) placing the at least one surgical instrument into the prostate via the reference plate at the placement coordinates determined from the positioning image.

6. The method according to claim 5 wherein, steps i) through viii) are repeated for a plurality of medical instruments.

7. The method according to claim 5 wherein, the method includes an additional step, concurrent with steps vi) and vii), of indicating and inputting to the processing means, via a graphical user interface, the target location and insertion path over the positioning image.

8. The method according to claim 5 wherein the method includes a further step, concurrent with step viii), of monitoring placement of the at least one medical instrument along the insertion path to the target location, via the placement coordinates, with one or more images generated by the three-dimensional ultrasonographic imaging system.

9. A system, employed in combination with a three-dimensional ultrasonographic imaging system, for assisting in the placement of at least one medical instrument into a prostate comprising:
    a reference means;
    a mounting means for mounting the reference means in a predetermined relationship to a transrectal ultrasonographic transducer;

the reference means including a plurality of apertures arranged in an predefined manner and sized to permit a medical instrument to pass therethrough;

a processing means for determining the spatial relationship between a three dimensional ultrasonographic image of the prostate generated via the transrectal ultrasonographic transducer and the reference means;

wherein the processing means merges a representation of the plurality of apertures with the three dimensional ultrasonographic image to assist in the placement of the at least one medical instrument in the prostate via an appropriate aperture.

10. A system according to claim 9 wherein the predefined manner of arranging the plurality of apertures forms a Cartesian coordinate grid.

11. A system according to claim 9 wherein the predefined manner of arranging the plurality of apertures is a polar coordinate grid.

12. A system according to claim 9 wherein the mounting means is attached between the transrectal ultrasonographic transducer and the reference means.

13. A system according to claim 9 wherein the reference means comprises a rectangular plate.

14. A system according to claim 9 wherein the plurality of apertures are provided with an index marking scheme to assist in the identification of placement coordinates and the selected aperture.

15. A system according to claim 9 wherein the mounting means includes a transverse adjustment means for adjusting the reference means transversely relative to a long axis passing through the transrectal ultrasonographic transducer.

16. A system according to claim 9 wherein the at least one medical instrument is a biopsy needle.

17. A system according to claim 9 wherein the at least one medical instrument is a guidance sheath.

18. A system according to claim 9 wherein the at least one medical instrument is a cryosurgical transducer.

19. A system according to claim 9 wherein the at least one medical instrument is a thermocouple device.

20. A system according to claim 9 wherein the processing means forms an integral portion of the three-dimensional imaging system.

21. A system according to claim 9 wherein the processing means is a stand-alone computer.

22. A system according to claim 9 wherein the processing means is a Macintosh workstation.

* * * * *

UNITED STATES PATENT AND TRADEMARK OFFICE
CERTIFICATE OF CORRECTION

PATENT NO. : 6,423,009 B1
DATED : July 23, 2002
INVENTOR(S) : Downey et al.

It is certified that error appears in the above-identified patent and that said Letters Patent is hereby corrected as shown below:

<u>Title page,</u>
Item [75], Inventor, add an inventor as follows: -- Gary Onik, Orlando, FL --

Signed and Sealed this

Tenth Day of August, 2004

JON W. DUDAS
*Acting Director of the United States Patent and Trademark Office*